US008354505B2

(12) United States Patent
Ristol Debart et al.

(10) Patent No.: US 8,354,505 B2
(45) Date of Patent: Jan. 15, 2013

(54) PROCESS FOR OBTAINING A CONCENTRATE OF VON WILLEBRAND FACTOR OR A COMPLEX OF FACTOR VII/VON WILLEBRAND FACTOR AND USE OF THE SAME

(75) Inventors: Pere Ristol Debart, Sabadell (ES); Maria Mercedes Faro Tomas, Sabadell (ES); Juan Ignacio Jorquera Nieto, Ametlla del Valles (ES)

(73) Assignee: Grifols, S.A., Barcelona (ES)

( * ) Notice: Subject to any disclaimer, the term of this patent is extended or adjusted under 35 U.S.C. 154(b) by 479 days.

(21) Appl. No.: 12/349,604

(22) Filed: Jan. 7, 2009

(65) Prior Publication Data

US 2009/0176709 A1     Jul. 9, 2009

(30) Foreign Application Priority Data

Jan. 8, 2008   (ES) .................................. 200800021

(51) Int. Cl.
*A61K 35/14*     (2006.01)
*A23J 1/06*     (2006.01)
(52) U.S. Cl. .......................... 530/383; 530/412; 530/414
(58) Field of Classification Search .................. None
See application file for complete search history.

(56) References Cited

U.S. PATENT DOCUMENTS

| 6,953,837 | B2 | 10/2005 | Mitterer et al. | |
|---|---|---|---|---|
| 7,005,502 | B1 | 2/2006 | Schwarz et al. | |
| 7,888,476 | B2 * | 2/2011 | Martel et al. | 530/383 |
| 7,932,355 | B2 * | 4/2011 | Chtourou et al. | 530/383 |
| 2006/0003921 | A1 | 1/2006 | Schwarz et al. | |

FOREIGN PATENT DOCUMENTS

| EP | 0411810 A1 | 2/1991 |
|---|---|---|
| EP | 0 860 444 A | 8/1998 |
| EP | 1632501 | 3/2006 |
| WO | WO 9322337 A1 | 11/1993 |
| WO | WO9931138 A1 | 6/1999 |
| WO | WO2005040214 | 5/2005 |
| WO | WO 2005040214 A1 | 5/2005 |

OTHER PUBLICATIONS

Search Report issued Jan. 8, 2008 by Spanish Patent Office in ES 200800021.
Chtourou, S. et al., "A Solvent/Detergent-treated and 15-nm Filtered Factor VIII: A New Safety Standard for Plasma-derived Coagulation Factor Concentrates," Vox Sanguinis (2007) vol. 92, pp. 327-337.
Furuya, K. et al., "Implementation of a 20-nm Pore-size Filter in the Plasma-derived Factor VIII manufacturing Process," Vox Sanguinis (2006) vol. 91, pp. 119-125.
Barington, K.A. et al., "A Very-high-purity von Willebrand Factor Preparation Containing High-molecular-weight Multimers," Vox Sanguinis 1999 vol. 76, pp. 85-89.

Behrmenn K. et al., *Thromb Haemost*, "Von Willebrand Factor Modulates Factor VIII Immunogenicity: Comparative Study of Different Factor VIII Concentrates in a Haemophilia A Mouse Model" vol. 88 (2002) pp. 221-229, Schattauer GmbH, Stuttgart.
Bjorkman S et al., "Pharmacokinetics of Coagulation Factors: Clinical Relevance for Patients with Haemophilia", *Clin Pharmacokinet* vol. 40(11) (2001) pp. 815-832.
Cejka *J. Clin Chem.*, "Enzyme Immunoassay for Factor VIII-Related Antigen" vol. 28, No. 6 (1982) pp. 1356-1358.
Gensana M. et al., *Hemophilia*, "Influence of von Willebrand Factor on the Reactivity of Human Factor VIII Inhibitors with Factor VIII" vol. 7 (2001) pp. 369-374.
Goudemand J. et al., *Blood*, "Influence of the Type of Factor VIII Concentrate on the Incidence of Factor VIII Inhibitors in Previously Untreated Patients with Severe Hemophilia A", vol. 107, No. 1, (2006) pp. 46-51, The American Society of Hematology.
Heath et al., "Standardisation of Factor VIII—V. Calibration of the 2nd International Standard for Factor VIII and von Willebrand Factor Activities in Plasma," *Thromb Haemost* vol. 68(2) (1992) pp. 155-159.
Kasper, C.K. Brooker, M. *Registry of Clotting Factor Concentrates*, (Jan. 2006).
Metzner et al., *Haemophilia*, "Characterization of Factor VIII/von Willebrand Factor Concentrates Using a Modified Method of von Willebrand Factor Multimer Analysis" vol. 4, Suppl. 3, (1998) pp. 25-32, Blackwell Science Ltd.
Ristol, P. et al. Sangre "Desarrollo y Caracterization de un Concentrado de Factor VIII Humano de Alta Pupreza, Sometido a dos Tratamientos Especificos de lnactivacion viral (Fanhdi®)", vol. 41 (1996) pp. 125-130.
Ruggeri at al., *Blood*, "The Complex Multimeric Composition of Factor VIII/von Willebrand Factor" vol. 57, No. 6 (1981) pp. 1140-1143, Grune & Stratton, Inc.
Siedlecki et al., *Blood*, "Shear-Dependent Changes in the Three-Dimensional Structure of Human von Willebrand Factor", vol. 88, No. 8 (1996) pp. 2939-2950. The American Society of Hematology.
Toole, J.J. et al., "Molecular Cloning of a cDNA Encoding Human Antihaemophilic Factor," *Nature* vol. 312 (1984) pp. 342-347.
Wood W.I. et al., "Expression of Active Human Factor VIII From Recombinant DNA Clones", *Nature* vol. 312 1984 330-337.
English language abstract for: Ristol. P et al. Sangre "Desarrollo y Caracterization de un Concentrado de Factor VIII Humano de Alta Pupreza, Sometido a dos Tratamientos Especificos de Inactivacion viral (Fanhdi©)", vol. 41 (1996) pp. 125-130.
European Search Report issued Apr. 20, 2009 in corresponding EP Appln No. 08380326.
Mazurier C. et al., "In vitro Study of a Triple-Secured von Willebrand Factor Concentrate", *Vox Sanguinis*, vol. 86, pp. 100-104 (2004).
J.C. Giddings "Molecular Genetics and Immunoanalysis in Blood Coagulation" *Ellis Horwood Series in Biomedicine* (1988) p. 77, Weinheim, F.R.G. : VCH ; Chicester, England : E. Horwood ; New York : Distributor, VCH publishers, 1988.
Theodore S. Zimmerman et al., "Factor VIII Procoagulant Protein" *Clinics in Haematology* vol. 14, No. 2, Jun. 1985, pp. 343-358.

* cited by examiner

*Primary Examiner* — Marsha Tsay

(57) ABSTRACT

A concentrate of Von Willebrand Factor (VWF) or a complex of Factor VIII/VWF is prepared by creating a solution of VWF or a complex of Factor VIII/VWF containing VWF at a concentration of up to 12 IU VWF:RCo/ml and a VWF/Factor VIII ratio of 0.4 or more; and nanofiltering that starting solution through a filter of pore size of 35 nanometers or smaller. The resulting VWF retains high molecular weight multimers.

11 Claims, 1 Drawing Sheet

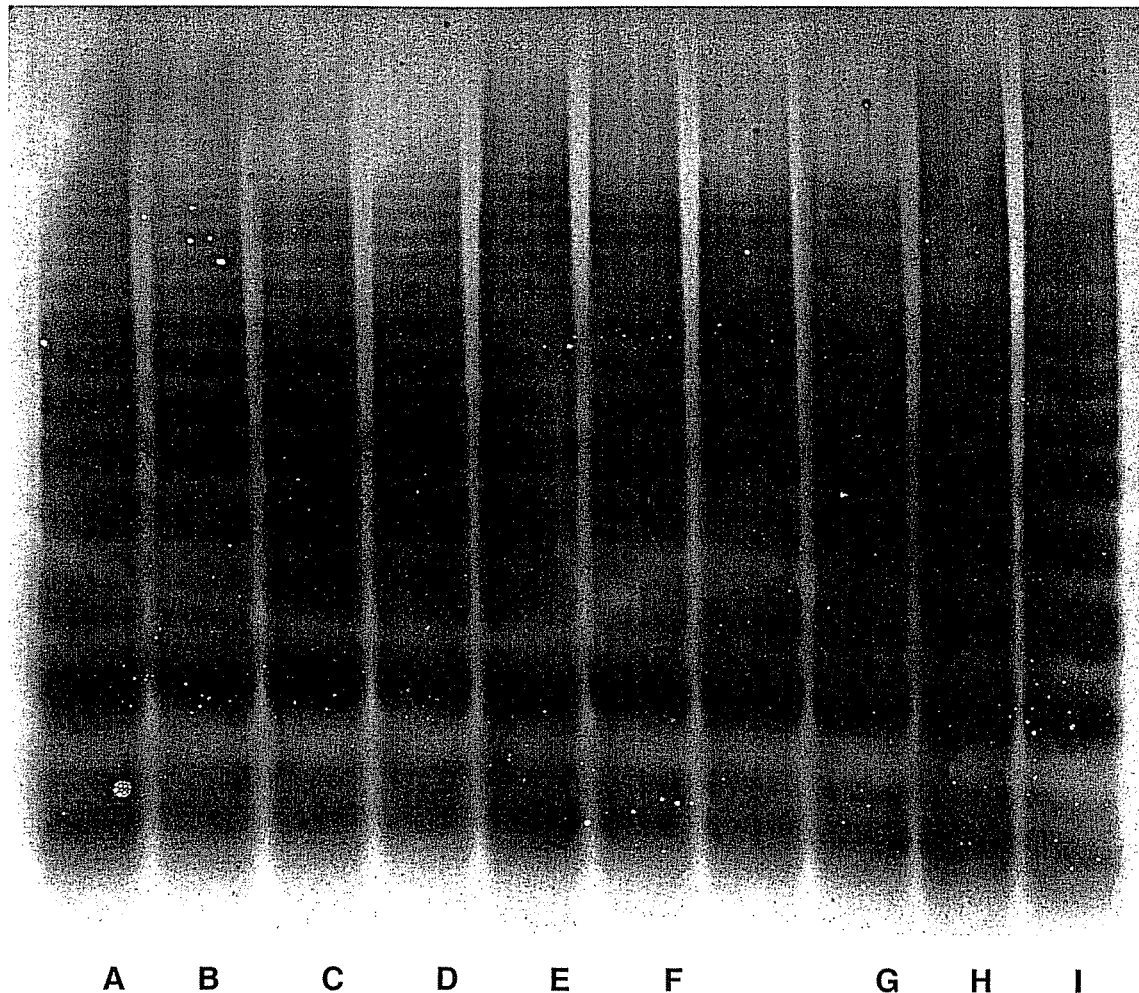
A, C, E, G, I: Non-nanofiltered product
B, D, F, H, J : Nanofiltered product

PROCESS FOR OBTAINING A CONCENTRATE OF VON WILLEBRAND FACTOR OR A COMPLEX OF FACTOR VIII/VON WILLEBRAND FACTOR AND USE OF THE SAME

1—SCOPE OF THE INVENTION

This invention relates to a therapeutic concentrate of Von Willebrand Factor or a complex of Factor VIII/Von Willebrand Factor and a process for the preparation of a medicinal compound indicated for the treatment of Von Willebrand's Disease (VWD) and Haemophilia A which has been nanofiltered through a pore size of less than 35 nm, through which viruses with and without an envelope such as, for example, hepatitis A or erythrovirus B19 can be effectively eliminated.

2—PRIOR ART

Von Willebrand's Factor (VWF) is a plasma protein having a multimer structure in which the molecular weight of the various forms varies between approximately 230000 Daltons (Da) for each monomer subunit and up to more than 20 million Da in the multimer forms of greater molecular weight, thus forming the largest known soluble protein. Its plasma concentration is approximately around 5-10 µg/ml [Siedlecki et al., Blood, vol 88, n 8, 1996: 2939-2950] and the plasma form of smaller size is that corresponding to the dimer, with an approximate size of 500000 Da.

VWF has an essential role to play in primary haemostasis, being responsible for the adhesion of platelets to damaged vascular surfaces and therefore formation of the platelet plug on which the mechanisms for formation of the fibrin coagulate develop. It is suggested that the higher molecular weight multimers support platelet adhesion mechanisms to the subendothelium with greater efficiency and the clinical efficacy of VWF concentrates has been related to the concentration of these multimers of higher molecular weight [Metzner et al., Haemophilia (1998) 4, 25-32].

In addition to this, in plasma VWF plays the part of a transporter and stabiliser of Factor VIII (FVIII), the FVIII molecule in the native state being found joined to multimer forms of VWF. The complex of Factor VIII/Von Willebrand Factor (FVIII/VWF) reaches a length of up to 1150 nm [Furuya K et al., Vox Sanguinis (2006) 91, 119-125]. In addition to this VWF in its smaller globular form will have a size of approximately 149×77×3.8 nm and can vary its structure, depending upon the shear force, into an extended or linear form [Siedlecki et al., Blood (1996) 88, 2939-2950]. The plasma concentration of FVIII is approximately around 0.05-0.1 µg/ml (that is some 50 to 100 times less than that of VWF).

Quantitative or qualitative defects in VWF produce changes in primary haemostasis, known as Von Willebrand's Disease, which is manifested as bleeding problems.

Purified VWF concentrates and FVIII concentrates with a high functional VWF content are of therapeutic use in the treatment of Von Willebrand's Disease.

Another aspect which has to be considered is that as VWF is the natural stabiliser for FVIII, concentrates of FVIII with a high VWF content may have many advantages when used in the treatment of Haemophilia A, as pointed out by a number of authors, for example: a longer mean in vivo life for infused FVIII, a protective effect against FVIII inhibitor antibodies [Gensana M. et al., Haemophilia, (2001) v. 7, 369-374] [Bjorkman S. et al., Clin Pharmacokinet, (2001) v. 40, 815-832] [Behrmann K. et al., Thromb Haemost, (2002) v. 88, 221-229] and a possible lesser frequency of the development of antibodies inhibiting FVIII activity [Goudemand J. et al., Blood (2006) 107: 46-51].

Analytical techniques for characterising both the content and the activity of VWF in these concentrates have been established. The determination of VWF activity as a cofactor of Ristocetin (VWF:RCo) is a widely used method for determining the activity of VWF [Heath et al., Thromb Haemost 1992; 68:155-159]. Measurement of VWF antigen (VWF: Ag) [Cejka J. Clin Chem. 1982; 28:1356-1358] shows us the quantity of both active and inactive VWF in a sample.

One of the relevant parameters for estimating the functional quality of VWF concentrates is the relationship between VWF:RCo activity and VWF:Ag antigen.

Given the possible importance of the multimer structure of VWF and the high molecular weight multimers in relation to its clinical activity and efficacy, characterisation of this multimer structure is fundamental to determining the usefulness of VWF concentrates and FVIII concentrates with a high VWF content. This multimer structure is determined by gel electrophoresis [Ruggeri et al., Blood 1981; 57: 1140-1143].

Various methods of purifying VWF or FVIII/VWF complex in which the VWF is functional and has a sufficient concentration for its use as a therapeutic product in VWD have been described, as shown by patents EP 0411810 and EP 0639203 or the publication by Ristol P. et al., Sangre (1996) 41:125-130.

Other FVIII purification processes provide a final product without VWF or only a trace quantity of the latter. These concentrates are not suitable for the treatment of VWD. Also in some cases the residual VWF present in these FVIII concentrates is not functional, having lost part of the multimers which form it, especially those of greater molecular weight. These concentrates will not have the advantages of FVIII concentrates which are rich in VWF when used for the treatment of Haemophilia A.

Existing FVIII concentrates are reported (Tables 2 and 3) in the record of coagulation factor concentrates created in 1997 and brought up to date by the World Haemophilia Federation (WHF) in 2006 (Kasper, C. K.; Brooker, M. Registry of clotting factor concentrates, January 2006), specifying among other things the methods of fractionation and viral inactivation, and their VWF content and functional effectiveness.

Among the nanofiltered concentrates of FVIII we must make a distinction between those which are nanofiltered through 35 nm (or larger pore size), and those in which this nanofiltration is not effective against viruses not having an envelope, such as for example hepatitis A virus (approximately 24 nm) or B19 virus (between 18 and 24 nm). On the other hand nanofiltered FVIII concentrates having pore sizes of less than 35 nm have no VWF content, or if they do have it, it lacks the high molecular weight multimers, as a result of which they are not effective for the treatment of VWD and do not have the advantages of FVIII concentrates rich in VWF when used for the treatment of Haemophilia A.

A great capacity for the removal of pathogenic agents is essential for ensuring the safety of biological products, and therefore various methods are incorporated into production processes with this aim. Among these mention should be made of chemical inactivation treatments based on the action of organic solvents associated with a detergent, which have demonstrated great effectiveness against viruses with a lipid envelope, although they are ineffective against viruses without a lipid envelope. Other physical treatments such as heat treatments are effective regardless of whether a lipid envelope is present or not, but their effectiveness depends on the severity of the treatment, which is in turn governed by the resistance of the protein being processed to inactivation. Other techniques which help to reduce viral load comprise separations by precipitation or chromatography.

One method which has proved to be very effective in eliminating viruses, regardless of whether or not a lipid envelope is present, is filtration through filters having a pore size capable of holding back viral particles (nanofiltration). This method has also been shown to be effective in the removal of other infectious particles such as prions. Despite this, the efficacy of this method is governed by the pore size used, which is essentially governed by the size of the protein which has to be filtered.

There are nanofilters of different pore sizes, normally between 15 and 75 nanometers (nm) and in general the smaller the pore size the greater the effectiveness in retaining pathogens, nanofilters of pore size below 35 nm and preferably between 15 and 20 nm being those which hold back the smallest viruses of size between 18 and 23 nm, such as erythrovirus B19 or hepatitis A virus (approximately 24 nm). Because of their characteristics these nanofilters will only be physically applicable to proteins of smaller size which can therefore be filtered with acceptable recovery for industrial production (normally post-nanofiltration recovery should be 60% or more).

Because of its molecular structure VWF or FVIII/VWF complex does not appear in principle to be capable of filtration by nanofilters smaller than 35 nm, especially the multimer forms of VWF of higher molecular weight. Hitherto nanofiltration of VWF or FVIII/VWF complex including multimer forms of higher molecular weight by nanofilters of less than 35 nm has not been possible.

From the Register of Coagulation Factor Concentrates of the World Haemophilia Federation (WHF) mentioned above, one nanofiltered FVIII concentrate (in this case using 20 nm) is the Cross Eight M of the Japanese Red Cross, which is also described in the publication by K. Furuya et al., Vox Sanguinis (2006) 91, 119-125. Despite the fact that it is stated in the publication that filtration of the VWF content of FVIII concentrate by 20 nm was achieved and that its multimer structure was not altered, we can see from the WHF register that this concentrate has a non-functional VWF. Going back to the Furuya publication we see that the VWF content is at trace level [page 123: . . . the VWF contents were similar to those usually found (0.007-0.015 U of VWF/U of FVIII:C) . . . ], whereas the ratio in plasma is 1 activity unit of VWF for each activity unit of FVIII (proportion 1:1). On the other hand characterisation of the multimer structure of this residual VWF (FIG. 4, page 123) shows no more than 10 multimer bands, whereas it is known that a well-preserved multimer structure which has the high molecular weight multimers must contain not less than 11 bands (Metzner et al., Haemophilia (1998) 4; page 27, 2nd paragraph). What Furuya tells us in his publication is that FVIII concentrate purified by affinity chromatography using monoclonal antibodies has a trace level of VWF content, that only the lower molecular weight multimers are preserved, and that this VWF composition is not adversely affected by nanofiltration at 20 nm. Obviously this concentrate (Cross Eight M) is unsuitable for the treatment of VWD and does not benefit from the presence of VWF in the proportions (1:1) found in normal human plasma.

The other nanofiltered FVIII concentrate mentioned in the register of coagulation factor concentrates of the World Haemophilia Federation referred to above is LFB's FACTANE. According to the register this concentrate is nanofiltered at 15 nm and contains VWF. This product corresponds to that obtained according to patent WO2005040214 which describes a FVIII composition nanofiltered through a sieve of pore size between 13 and 25 nm in which the efficiency of virus retention is associated with a high molecular weight VWF content (more than 10 multimers) of less than 15%, again confirming what was observed in Furuya's publication, that multimers of VWF of lower molecular weight can be nanofiltered through 20 nm when low concentrations are present with respect to FVIII, that is to say with VWF/FVIII ratios which are far from 1 (0.015 in the case of Furuya and 0.15 in the case of Factane, patent WO2005040214). Conversely multimers of greater molecular weight are retained by the nanofilter. Furthermore, in this patent, in order to recover the FVIII associated with the VWF, which would also be retained, a forced dissociation of the FVIII/VWF complex is brought about through the addition of $CaCl_2$ in a concentration greater than 0.20 M, which is the minimum concentration at which the FVIII/VWF complex dissociates. Despite this, all the examples made use of a $CaCl_2$ concentration of at least 0.35 M to ensure dissociation of the FVIII/VWF complex, and thereby the recovery of FVIII. The composition defined in this patent is solely for the purpose of treating FVIII deficit and not VWD. Also this product is not suitable for the treatment VWD, as is proven in the product authorisation from the "French Agency for the Safety of Health Products" [http://afssaps-prd.afssaps.fr/php/ecodex/frames.php?specid=66716833&typedoc=R&ref=R0093176.htm], in section 4.1 Therapeutic Indications, where it is clearly specified that the product does not contain VWF in sufficient quantity for the treatment of VWD. In addition to this, in the publication on that product [Vox Sanguinis (2007) 92, 327-337] the authors confirm that the product (Factane) is not intended for the treatment of VWD (page 335).

To sum up, the aim of the procedures described by K. Furuya et al., [Vox Sanguinis (2006) 91, 119-125] and patent WO2005040214 and the Vox Sanguinis (2007) 92, 327-337 publication is to obtain a FVIII concentrate which is poor in VWF (<15% or a VWF/FVIII ratio of <0.15:1) applicable to the treatment of Haemophilia A, but which does not benefit from the advantages which a concentrate rich in VWF would provide for the treatment of Haemophilia, and which in no circumstances would be suitable for the treatment of VWD.

It has been stated (Siedlecki et al., Blood, vol 88, n 8, 1996: 2939-2950) that VWF changes its three-dimensional structure under flow conditions giving rise to high shear forces (high shear stress), which allows platelet adhesion mechanisms to occur in vivo. This change in structure has the result that the molecule changes from being a globular structure to a more linear form. In this respect K. Furuya et al., in their publication (Vox Sanguinis (2006) 91, 119-125) have already indicated that the filtration of their FVIII concentrate through 20 nm must be carried out at high pressure (0.8 bar) in order to obtain an acceptable yield of FVIII, and this they suggest is probably due to the fact that at lower pressure the flow effect is not sufficient for the VWF present to change its structure, thus making filtration difficult. Under the specified conditions (0.8 bar) they also achieved good recovery of the low molecular weight VWF multimers present, bearing in mind that the starting values prior to nanofiltration are very low.

The documents cited do not disclose the possible application of nanofiltration through less than 35 nm, such as for example through 20 nm, to VWF or VWF/FVIII complex (ratio $\geq 0.4$) with a functional content of high molecular weight multimers which will enable it to be used for the treatment of VWD, or which maintains the advantages described of concentrates rich in VWF when used for the treatment of Haemophilia A. Furthermore, WO2005040214 clearly indicates to those skilled in the art that this pore size impedes the passage of high molecular weight VWF.

The state of the art in which the nanofiltration of VWF as a therapeutic product is at the present time restricted to nanofiltration through 35 nm is demonstrated by patent EP1632501. This patent discloses a process for obtaining a VWF concentrate with a low FVIII content (FVIII:C/VWF:RCo ratio less than 0.06) which includes a stage of virus removal by nanofiltration through filters of 35 nm pore size, as indicated in paragraph 23 of the description, and in Example 1, paragraph 37. From this patent we can learn that nanofiltration of a molecule of the size of VWF is not feasible for nanofilters having a pore size of less than 35 nm.

As we have seen, at the present time there is no therapeutic concentrate indicated for the treatment of Von Willebrand's disease which has been nanofiltered through 20 nm. In addition to this the present state of the art indicates that this nanofiltration of VWF containing high molecular weight multimers through 20 nm is not possible, as in the case of the FVIII/VWF molecular complex, if the high molecular weight multimers of VWF are present and the proportion between VWF and FVIII is greater than 0.15.

The preparation of a FVIII/VWF concentrate nanofiltered through 20 nm with proportions between the two components of the FVIII and VWF macromolecular complex which are more similar to those normally encountered in human plasma (1 unit of VWF for every 1 unit of FVIII), which still has all the advantages of the native FVIII/VWF complex and is suitable for the treatment of VWD and Haemophilia A, is still an unresolved problem.

The processes for obtaining VWF or FVIII/VWF complex from human plasma normally start with the cryoprecipitate fraction, and purify by selective precipitation or more recently by chromatographic techniques, essentially using ion exchange and/or affinity.

Processes for the purification of FVIII which are currently based on immunoaffinity chromatography (using monoclonal antibodies) provide a FVIII with a very high specific activity but lack functional VWF [K. Furuya et al., Vox Sanguinis (2006) 91, 119-125].

As we have seen, these processes for obtaining VWF or the FVIII/VWF complex involve one or more specific stages of virus inactivation or removal.

In this invention the activity of the VWF is based on the role of VWF as a cofactor for the antibiotic Ristocetin (VWF: RCo) in its ability to induce platelet aggregation (Pharmacopoiea Europea 07/2006:20721). This activity is expressed in International Units (IU VWF:RCo) and its concentration in IU/milliliter (IU VWF:RCo/ml).

The activity of FVIII relates to the coagulating activity of FVIII (FVIII:C) which is based on the role of FVIII as a cofactor in the activation of FX in the presence of FIXa, calcium ions and phospholipids (Pharmacopoeia Europea 07/2006:20704). This is quantified for a chromogenic substrate and expressed in International Units (IU FVIII) and its concentration in IU FVIII/milliliter (IU FVIII/ml).

3—DESCRIPTION OF THE INVENTION

This invention describes a therapeutic concentrate of Von Willebrand Factor or a complex of Factor VIII/Von Willebrand Factor which has been nanofiltered through a sieve of pore size less than the equivalent to 35 nm in which the product obtained has VWF:RCo/FVIII:C ratio which is greater than or equal to 0.4 and a conserved multimer structure for the VWF which includes the high molecular weight multimers (more than 11 bands) and which is useful for the preparation of a medicinal compound indicated for the treatment of Von Willebrand's Disease and Haemophilia A, and a process for obtaining it.

On the basis of investigations carried out into the nanofiltration of VWF or the FVIII/VWF complex in which the VWF has a preserved multimer structure containing the high molecular weight multimers, the inventors have surprisingly demonstrated that in the case of a solution containing VWF or the FVIII/VWF complex and calcium ions it is possible to perform filtration through a nanofilter of nominal pore size less than 35 nm and preferably 20 nm at a maximum pressure of less than 0.5 bar and preferably between 0.2 and 0.4 bar.

The solution which is to be nanofiltered has a maximum concentration of 0.6 Absorbance Units ($AU_{280}$), equivalent to not more than 12 IU VWF:RCo/ml. The protein composition of the solution, in addition to its own VWF and FVIII content, may also comprise other proteins, such as for example fibrinogen or fibronectin, the specific activity of the VWF (IU VWF:RCo/mg protein) being greater than or equal to 1 and typically 10 or more. The specific activity of the FVIII (IU FVIII/mg protein) in the case of nanofiltration of the FVIII/VWF complex is also greater than or equal to 1, and typically 10 or more.

The solution which has to be nanofiltered may contain calcium (chloride) between 0.05 and 0.20 M and at least one basic amino acid as a protein stabiliser, preferably histidine, between 20 and 30 mM. The pH of the solution which has to be filtered must be greater than 5.5 in order to prevent denaturation.

The load ratio, expressed as the biological activity of the protein which has to be filtered, can reach 50 IU of VWF:$RCo/cm^2$ of filtering surface area, equivalent to 0.5 mg of $VWF/cm^2$.

Under the conditions specified it is possible to filter up to 120 liters of solution per $m^2$ of filtering surface area, obtaining a recovery of FVIII activity of more than 70% and a recovery of VWF activity of more than 60%, with a preserved VWF multimer structure (more than 11 multimers) and a VWF:RCo/FVIII ratio which is at least 80% of that of the material used.

The solution which has to be filtered is characterised in that it has a VWF:RCo/FVIII activity ratio which is greater than or equal to 0.4 and typically between 1 and 3, and is therefore equally applicable to solutions of VWF without FVIII and solutions of the FVIII/VWF complex, given that VWF, being the multimer molecule of larger size, is the one which limits the process.

Under the specified conditions the standard filtration flow is a maximum of 30 liters/hour/$m^2$, and typically between 10 and 20 liters/hour/$m^2$, the filtration time being 12 hours or less. This makes industrial application possible, and it is obvious that these parameters can be changed or optimised by varying the nanofiltration surface area, this being the factor which limits the process, because of its high cost.

In a preferred embodiment pre-filtration is carried out using a nanofilter of pore size between 35 and 100 nm prior to nanofiltration through a pore size of less than 35 nm. The ratio between the areas of the prefilter and the nanofilter (<35 nm) lies between 1:2 and 1:4.

It is also possible to carry out a double nanofiltration through 20 nm (20 nm+20 nm), which increases the benefit of added safety for the nanofiltration product.

Through this invention a nanofiltered VWF or FVIII/VWF complex is obtained which makes it possible to prepare a high purity medication suitable for the treatment of VWD and Haemophilia A, having a VWF activity of more than 100 IU VWF:RCo/ml and a ratio between the VWF and FVIII activities of 0.4 or more, and in which the multimer structure of the VWF includes the high molecular weight multimers (more than 11 bands).

4—EXAMPLES

Of the nanofilters commercially available, Planova® nanofilters from Asahi Kasei Corporation, Japan, manufactured from regenerated cellulose and having a pore size of approximately 35±2 nm in the case of Planova 35N and 19±1 nm in the case of Planova 20N, were used to provide examples of the invention. Filters of this type allow dead end mode and tangential mode filtration. In the examples which follow nanofiltration using Planova was carried out in dead end mode, but for the purposes of this invention use of tangential mode is also suitable, as is the use of nanofilters of other commercial brands and composition, which will be known to those skilled in the art. Both the assembly, the method of operation and the testing to ensure that the nanofilters to which this invention relates are intact are specified in full in the manufacturer's instructions.

Example 1

Acquisition of the Starting Material

The solution of FVIII/VWF complex prior to nanofiltration, originating from human plasma, can be obtained, for example, from the solubilised cryoprecipitate by precipitation with polyethylene glycol and subsequent purification with affinity chromatography, as shown in patent EP 0411810. The nanofiltered solution can be subsequently purified to obtain a high purity product, for example by precipitation with glycine, as shown in patent EP 0639203. Alternatively, the FVIII or VWF, or both, may be obtained by biosynthesis using recombinant DNA technology in transgenic cells or animals [Wood W. I. et al., Nature (1984) 312: 330-337]; [Toole, J J. et al., Nature (1984) 312: 342-347].

Example 2

Nanofiltration of the FVIII/VWF Complex

Serial filtration through a Planova 35N filter of 0.12 m² and a Planova 20N filter of 0.3 m² was carried out using 14.7 liters of a solution of partly purified FVIII/VWF complex having a specific activity of 10.4 IU FVIII/$AU_{280nm}$ and a VWF:RCo concentration of 5.69 IU/ml, equivalent to 0.235 $AU_{280nm}$, in the presence of 25 mM histidine and 0.14 M calcium at a pH of 6.77 and a temperature of 20±5° C. Filtration was carried out at a constant flow of approximately 14 L/h/m², maintaining a pressure difference of between 0.20 and 0.30 bar in the Planova 20N throughout filtration of all of the solution, which was completed in a time of 3.3 hours. The productivity per area and time unit was 3.6 IU FVIII/cm²/hour, 8.2 IU VWF RCo/cm²/hour (VWF:RCo/FVIII:C ratio=2.3) and 9.8 IU VWF:Ag/cm²/hour. Recovery of activity was 94% of FVIII and 95% of VWF RCo.

Example 3

Characteristics of the FVIII/VWF Complex Nanofiltered Through Planova 20N 7 different lots of starting material were processed in the manner illustrated in Example 2. FVIII/VWF complex having a specific activity close to or greater than 10 IU FVIII/$AU_{280nm}$ and a protein concentration of 0.3±0.2 $AU_{280nm}$ was used as the starting material in the presence of 25 mM histidine and 0.14 M of calcium at a pH of 6.8±0.2 and a temperature of 20±5° C. In one embodiment, the solution containing VWF or the FVIII/VWF complex has a calcium ion ($Ca^{++}$) concentration of about 0.05-0.2 M. Clarification through 0.1 μm and subsequent serial nanofiltration through Planova 35N and Planova 20N was carried out. Filtration was maintained at a constant flow of between 10 and 20 liters/h/m². The operating pressure in the Planova 20N filter was maintained between 0.2 and 0.4 bar throughout the filtration in all cases.

The results obtained (Table 1) show that nanofiltration of FVIII/VWF complex through a pore size of 20 nm under the conditions specified has no effect at all on the activity and purity (specific activity) of the nanofiltrate obtained.

Comparative analysis of the VWF:RCo/FVIII and VWF:RCo/VWF:Ag ratios (Table 1) obtained in the material before and after nanofiltration makes it possible to establish that under the specified conditions it is possible to filter the VWF present in the FVIII/VWF concentrate through a sieve of 20 nm pore size without affecting the functionality of VWF as a cofactor of Ristocetin.

TABLE 1

CHARACTERISTICS OF THE FVIII/VWF COMPLEX BEFORE AND AFTER NANOFILTRATION

| SPECIFIC ACTIVITY | | | | Ratio | | Ratio | |
|---|---|---|---|---|---|---|---|
| (IU FVIII/$AU_{280}$) | | (IU VWF:RCo/$AU_{280}$) | | (VWF:RCo/FVIII) | | (VWF:RCo/VWF:Ag) | |
| BEFORE NANO-FILTRATION | AFTER NANO-FILTRATION | BEFORE NANO-FILTRATION | AFTER NANO-FILTRATION | BEFORE NANO-FILTRATION | AFTER NANO-FILTRATION | BEFORE NANO-FILTRATION | AFTER NANO-FILTRATION |
| 10.1 ± 2.9 | 9.4 ± 3.3 | 24.0 ± 8.2 | 24.1 ± 11.2 | 2.3 ± 0.5 | 2.3 ± 0.1 | 0.8 ± 0.06 | 0.9 ± 0.07 |

The values correspond to the mean of 7 lots ± SD

Example 4

Multimer Structure of the VWF Obtained by Gel Electrophoresis, Establishing Preservation of the Same, Including Multimers of Greater Molecular Weight with More than 11 Bands FIG. 1 shows the multimer structure of the VWF in different lots of final products, with and without the nanofiltration stage. At least 16 bands in lanes corresponding to the nanofiltered material can be counted in the original photograph.

Example 5

Effect of Pressure Difference on Nanofiltration of the FVIII/VWF Complex

A partly-purified solution of FVIII/VWF in which the specific activity of the FVIII was approximately 10 IU/$AU_{280}$ nm and with concentrations in the range 0.1-0.3 $AU_{280}$ nm was filtered through Planova 35N under the conditions described in Examples 2 and 3. Nanofiltration was set for high pressure (0.8 bar) and low pressure (0.3 bar), and the results shown in Table 2 were obtained.

TABLE 2

| | PROCESS CONDITIONS | PRESSURE (bar) | PROTEIN CONCENTRATION USED ($OD_{280\,nm}$) | FLOW RATIO % with respect to the initial flow | |
|---|---|---|---|---|---|
| | | | | After 1 HOUR | After 3 HOURS |
| PLANOVA 35N | HIGH PRESSURE | 0.8 | 0.179 | 10.6 | 7.9 |
| | | | 0.271 | 14.6 | n.a.[1] |
| | LOW PRESSURE (n = 5) | 0.3 | 0.187 ± 0.039 0.133-0.236 | 98.2 ± 7.3 92.1-110.8 | 88.6 ± 3.5 84.5-92.5 |

[1] not available given that the process was interrupted because of clogging and blocking of the nanofilter.

Likewise this solution of FVIII/VWF complex prefiltered through Planova 35N was filtered through Planova 20N under the conditions described in Example 2. Nanofiltration was set for high pressure (0.8 bar) and low pressure (0.3 bar), and the following results were obtained:

TABLE 3

| | PROCESS CONDITIONS | PRESSURE (bar) | PROTEIN CONCENTRATION USED ($OD_{280\,nm}$) | FLOW RATIO % with respect to the initial flow | |
|---|---|---|---|---|---|
| | | | | After 1 HOUR | After 3 HOURS |
| PLANOVA 20N | HIGH PRESSURE | 0.8 | 0.146 | 40 | n.a.[1] |
| | LOW PRESSURE (n = 4) | 0.3 | 0.199 ± 0.05 0.139-0.254 | 86.5 ± 9.9 75.7-98.4 | 75.7 ± 4.5 72.1-82.1 |

[1] not available given that the process was interrupted because of clogging and blocking of the nanofilter.

In filtration through Planova 35N at high pressure there was a drastic fall in the flow, only 10.6% and 14.6% of the initial flow being observed after one hours nanofiltration and, in one case, only 7.9% of the initial flow at 3 hours. In filtration through Planova 35N at a pressure difference of 0.3 bar the flow remained at 88.6% even after 3 hours' nanofiltration.

In filtration through Planova 20N, using a solution of FVIII/VWF complex prefiltered through Planova 35N as the starting material, and with a pressure difference of 0.8 bar, a flow ratio of 40% was obtained after one hour's nanofiltration and the filtration was stopped before 3 hours because of clogging of the filter. In filtration through Planova 20N with a pressure difference of 0.3 bar the flow remained at 75.7% even after 3 hours' nanofiltration.

It is clear from the above examples that maintaining low pressure conditions during filtration for pore sizes of 35 nm or below avoids the production of a sudden fall in flow. As a consequence, no blocking of part of the pores of the filter membrane due to the deposition of high molecular weight molecules present in the FVIII/VWF solution, such as multimer forms of VWF reaching sizes of up to 20000000 Da, was observed under these pressure conditions.

Example 6

Effect of the Concentration of the Material Used on Nanofiltration of the FVIII/VWF Complex Using different solutions of partially purified FVIII/VWF complex having a specific FVIII activity of approximately 10 IU FVIII/$AU_{280nm}$, with a VWF activity in relation to FVIII activity (VWF:RCo:FVIII) of approximately 2, and including concentrations in the range 0.1-0.65 $AU_{280nm}$, filtration was carried out through Planova 20N at a pressure difference of approximately 0.5 bar and under the same process and product composition conditions as described in Examples 1 and 2 (except for its concentration).

The results obtained are shown in Table 4:

TABLE 4

| | PROTEIN CONCENTRA-ION USED ($DO_{280nm}$) | FLOW RATIO (% with respect to the initial flow) | | RATIO USED ($AU_{280\,nm}/cm^2$ of P20N) | PRODUCTIVITY (Activity filtered per unit area of P20N and time)[2] | | PROTEIN RECOVERY ($OD_{280\,nm}$) (%) |
|---|---|---|---|---|---|---|---|
| | | After 1 HR | After 3 HRS | | IU FVIII/$cm^2$/h | IU FVW:RCo/ $cm^2$/h | |
| PLANOVA 20N | 0.106 | 80.7 | 71.4 | 1.77 | 2.6 | 5.2 | 77.6 |
| | 0.170 | 63.6 | 30.5 | 1.39 | 2.0 | 4.1 | 87.6 |
| | 0.314 | 60.7 | 33 | 2.85 | 3.9 | 7.8 | 82.5 |

TABLE 4-continued

| PROTEIN CONCENTRA-ION USED ($OD_{280nm}$) | FLOW RATIO (% with respect to the initial flow) | | RATIO USED ($AU_{280 nm}/cm^2$ of P20N) | PRODUCTIVITY (Activity filtered per unit area of P20N and time)[2] | | PROTEIN RECOVERY ($OD_{280 nm}$) (%) |
|---|---|---|---|---|---|---|
| | After 1 HR | After 3 HRS | | IU FVIII/$cm^2$/h | IU FVW:RCo/ $cm^2$/h | |
| 0.343 | 52.9 | 32 | 2.19 | 3.2 | 6.5 | 88.6 |
| 0.648 | 16.2 | nd[1] | 1.16 | 0.9 | 1.8 | 46.8 |

[1]n.d: not determined (because of prior blocking and clogging of the nanofilter).
[2]Values calculated on the basis of the quantity of protein filtered during 6 hours, with in all cases a specific activity of 10 IU FVIII/$AU_{280 nm}$, a VWF:RCo/FVIII ratio of 2 and the protein recovery observed in each case.

The reduction in flow observed during nanofiltration is directly proportional to the concentration of the loading material. Thus the flow observed after one hour's nanofiltration is 80.7%, 63.6%, 60.7%, 52.9% and 16.2% with respect to the initial flow for concentrations of 0.106 AU, 0.17 AU, 0.314 AU, 0.343 AU and 0.648 AU respectively. With regard to the flow observed after 3 hours' nanofiltration, the fall below values of some 30.5% of the initial flow can be attributed to the fact that nanofiltration was carried out under pressure conditions representing the upper limit for the process.

Optimum productivity values (7.8 IU of VWF:RCo/$cm^2$/h equivalent to 46.8 IU of VWF:RCo/$cm^2$) and protein recovery (see table) were obtained for a loading concentration of close to 0.3 AU. When the concentration of loading material is a maximum (0.648 AU) clogging of the filter is observed from the start of filtration and productivity and recovery values fall drastically to values below 2 IU of VWF:RCo/$cm^2$/h and 46.8% total protein recovery, a result which rules out nanofiltration at this concentration.

It can be established from these results that the viable concentration range for the nanofiltration of FVIII/VWF solution having a specific activity of approximately 10 IU FVIII/$AU_{280}$ nm is $\leq$0.6 AU, approximately equivalent to $\leq$6 IU/ml of FVIII and $\leq$12 IU/ml of VWF:RCo.

Example 7

Effect of Calcium Concentration on the Nanofiltration of FVIII/VWF Complex

Using different solutions of FVIII/VWF complex formulated with albumin having a specific activity of more than 10 IU FVIII/$AU_{280}$ and a FVIII activity of around 3 IU/ml, approximately equivalent to 4 IU/ml of VWF:RCo, filtration was carried out through a filter having a pore size of 20 nm in the presence of 0.1 M arginine, 25 mM histidine and 0.05 mM calcium at a pH of 7.3±0.1. Filtration was carried out maintaining a pressure difference across the Planova 20N of approximately 0.5 bar. Table 5 shows the most relevant parameters obtained in the tests carried out using two separate lots of product.

TABLE 5

| COMPOSITION OF THE MATERIAL USED | | PRODUCTIVITY (IU/$cm^2$/h) | | RECOVERY (%) |
|---|---|---|---|---|
| $OD_{280 nm}$ | FVIII (IU/ml) | FVIII | VWF:RCo | FVIII ACTIVITY |
| 0.143 | 2.77 | 1.6 | 2.0[1] | 43.3 |
| 0.188 | 2.96 | 1.6 | 2.0[1] | 46.6 |

[1]Values calculated on the basis of the IU of FVIII filtered per time and surface units considering a (VWF:RCo/FVIII) ratio of 1.24.

These results indicate that the virtual absence of calcium (0.05 mM) and its replacement by arginine (0.1M) produce a significant fall in productivity, down to values of 1.6 IU FVIII/$cm^2$/hour and 2.0 IU VWF:RCo/$cm^2$/hour in both cases, which are remarkably less than those observed in Example 2 (3.6 IU FVIII/$cm^2$/hour and 8.2 IU VWF:RCo/$cm^2$/hour), with a similar FVIII activity in the starting material.

Likewise the recovery of FVIII activity observed in the two tests fell to values of 43.3% and 46.6% respectively. Nevertheless, even under these conditions nanofiltration of the macromolecular complex of FVIII and VWF with proportions between the VWF and FVIII activities similar to those encountered in nature (1:1) is feasible.

Example 8

Production of a Lot of FVIII/VWF Nanofiltered on an Industrial Scale

Starting with a partly purified solution of FVIII/VWF complex originating from more than 3000 liters of plasma and having a specific activity of 15.6 IU FVIII/$AU_{280}$, filtration was carried out in series through a filter of nominal pore size of 35 nm (Planova 35N) of 4 $m^2$ and two filters having a nominal pore size of 20 nm (Planova 20N) of 4 $m^2$ in the presence of 25 mM histidine and 0.14 M calcium at pH 6.80. Filtration was carried out at a constant flow of approximately 107 L/h maintaining a pressure difference across the Planova 20N of between 0.20 and 0.35 bar, with an application load (product solution+post washing) of 120.2 kg/$m^2$ of Planova 20N. The total activity applied per unit area was 8.9 IU FVIII/$cm^2$ and 19.1 IU VWF:RCo/$cm^2$. Activity recovery from nanofiltration was 70.4% of FVIII and 77.3% of VWF:RCo. Including post-washing and after concentrating the nanofiltered product obtained the observed recovery of activity was 97.5% of FVIII and 86.8% of VWF:RCo.

Subsequent precipitation of sodium chloride and glycine (according to EP 0639203) yielded a high purity nanofiltered FVIII/VWF concentrate.

The high purity nanofiltered FVIII/VWF concentrate obtained was stabilised, and its strength was adjusted before the product was metered into bottles.

The relative VWF content in relation to the FVIII content, expressed as the VWF:RCo/FVIII ratio, over the purification process is shown in Table 6 below:

TABLE 6

Variation in activity (IU VWF:RCo/IU FVIII) in the purification process

|  | Nanofiltered product (n = 1) | Non-nanofiltered product (n = 6) |
|---|---|---|
| Starting material | 1.7 | 1.57 ± 0.19 |
| Intermediate concentrate | 1.9 | 1.71 ± 0.11 |
| High purity product | 1.5 | 1.14 ± 0.25 |
| Formulated high purity product | 1.5 | 1.24 ± 0.19 |

These results indicate that the use of nanofiltration in the process of purifying FVIII/VWF complex does not essentially affect the subsequent purification stage which leads to a high purity product. This therefore indicates that the conditions established for nanofiltration of the FVIII/VWF concentrate through a sieve of pore size of 20 nm does not adversely affect the proportion of the multimer forms of higher molecular weight of VWF, given that such a change would be expected to have an adverse effect on subsequent purification by precipitation.

The nanofiltered FVIII/VWF concentrate has a relative VWF concentration which is sufficient for use as a therapeutic product in VWD and a FVIII content which also enables it to be used for the treatment of Haemophilia A, with the additional benefit of the presence of quantities of VWF (the natural stabiliser of FVIII) similar to those found in nature, the beneficial properties of which in the treatment of Haemophilia A have been mentioned previously.

Although the invention has been described on the basis of preferred embodiments thereof and illustrated examples, it will be understood that on the basis of the material disclosed, those skilled in the art may introduce multiple variants into the embodiments of the invention, which will remain largely included therein, having regard to the content of the following claims and their equivalents.

The invention claimed is:

1. A process for obtaining a concentrate of a Factor VIII/Von Willebrand Factor (VWF) complex of human or recombinant origin, said process comprising:
   a) preparing a solution of a Factor VIII/Von Willebrand Factor complex which contains Von Willebrand Factor in a concentration of up to 12 IU VWF:RCo/ml and has a VWF:RCo/Factor VIII activity ratio of 0.4 to 3,
   b) a nanofiltration step consisting of filtering the solution prepared in a) through a nanofilter having pore sizes of less than 35 nanometers, at a maximum pressure of less than or equal to 0.5 bar, in the presence of calcium ion at a concentration between 0.05 and 0.14 M, and at a pH greater than 5.5;
   and thereby obtaining a concentrate of Factor VIII/VWF complex, wherein the VWF:RCo/Factor VIII activity ratio is not affected.

2. A process according to claim 1, wherein the Von Willebrand Factor recovered after nanofiltration maintains a multimer structure which includes multimers of the order of 11 or more.

3. A process according to claim 1, wherein the yield of recovered Von Willebrand Factor after nanofiltration is 60% or more.

4. A process according to claim 1, wherein the yield of recovered Von Willebrand Factor after nanofiltration is 70% or more.

5. A process according to claim 1, wherein a loading ratio of up to 50 IU of Von Willebrand Factor per $cm^2$ of filtering surface area is used.

6. A process according to claim 1, wherein the maximum concentration of the solution being filtered is 0.6 AU ($OD_{280}$).

7. A process according to claim 1, wherein the nanofiltration is carried out at a pressure of between 0.2 and 0.4 bar.

8. A process according to claim 1, wherein the standard nanofiltration flow is between 10 and 20 liters/hour/$m^2$.

9. A process according to claim 1, wherein the nanofiltration is carried out using a nanofilter having pore sizes of 20 nanometers or less.

10. A process according to claim 1, wherein the nanofiltration is carried out using a nanofilter having pore sizes of 19±1 nanometers.

11. A process according to claim 1, wherein the recovered concentrate of Factor VIII/VWF complex has a VWF:RCo/Factor VIII activity ratio of at least 80% of that of the solution prepared in a).

* * * * *